United States Patent
Ogata et al.

(10) Patent No.: US 7,592,122 B2
(45) Date of Patent: Sep. 22, 2009

(54) PHOTORESIST COMPOSITION, AND LOW-MOLECULAR COMPOUND AND HIGH-MOLECULAR COMPOUND FOR THE PHOTORESIST COMPOSITION

(75) Inventors: Toshiyuki Ogata, Kanagawa (JP); Kotaro Endo, Kanagawa (JP); Hiromitsu Tsuji, Kanagawa (JP); Masaaki Yoshida, Kanagawa (JP); Mitsuru Sato, Kanagawa (JP); Syogo Matsumaru, Kanagawa (JP); Hideo Hada, Kanagawa (JP)

(73) Assignee: Tokyo Ohka Kogyo Co., Ltd., Kanagawa (JP)

( * ) Notice: Subject to any disclaimer, the term of this patent is extended or adjusted under 35 U.S.C. 154(b) by 305 days.

(21) Appl. No.: 10/553,315

(22) PCT Filed: Apr. 15, 2004

(86) PCT No.: PCT/JP2004/005410

§ 371 (c)(1),
(2), (4) Date: Oct. 17, 2005

(87) PCT Pub. No.: WO2004/097525

PCT Pub. Date: Nov. 11, 2004

(65) Prior Publication Data

US 2006/0210913 A1   Sep. 21, 2006

(30) Foreign Application Priority Data

Apr. 28, 2003 (JP) ............................. 2003-124319
Nov. 20, 2003 (JP) ............................. 2003-391139

(51) Int. Cl.
*G03F 7/004* (2006.01)
*C08C 19/28* (2006.01)

(52) U.S. Cl. .............. 430/270.1; 430/287.1; 430/326; 430/907; 525/359.3

(58) Field of Classification Search .............. 430/270.1, 430/326, 907, 287.1; 525/359.3
See application file for complete search history.

(56) References Cited

U.S. PATENT DOCUMENTS

| | | | | |
|---|---|---|---|---|
| 5,558,971 A | 9/1996 | Urano et al. | ............... | 430/170 |
| 5,558,976 A | 9/1996 | Urano et al. | ............... | 430/326 |
| 5,558,978 A * | 9/1996 | Sch adeli et al. | ......... | 430/270.1 |
| 2002/0015906 A1 | 2/2002 | Lee et al. | ............... | 430/170 |
| 2002/0177067 A1 | 11/2002 | Kim | ............... | 430/270.1 |
| 2003/0082479 A1 | 5/2003 | Hatakeyama et al. | .... | 430/270.1 |
| 2003/0134224 A1 | 7/2003 | Mizutani et al. | ......... | 430/270.1 |
| 2003/0232277 A1* | 12/2003 | Sasaki et al. | ............. | 430/270.1 |
| 2004/0053161 A1* | 3/2004 | Kanna et al. | ............. | 430/270.1 |

FOREIGN PATENT DOCUMENTS

| | | |
|---|---|---|
| JP | 8-123032 | 5/1996 |
| JP | 2002-53618 | 2/2002 |
| JP | 2002-90997 A | 3/2002 |
| JP | 2002-091001 | 3/2002 |
| JP | 2002-145962 A | 5/2002 |
| JP | 2002-201219 | 7/2002 |
| JP | 2002-333715 A | 11/2002 |
| JP | 2002-338634 A | 11/2002 |
| JP | 2003-15300 | 1/2003 |
| JP | 2003-15301 A | 1/2003 |
| JP | 2003-57826 A | 2/2003 |
| JP | 2003-89708 A | 3/2003 |
| JP | 2003-252928 | 9/2003 |
| WO | 00/67072 | 11/2000 |
| WO | 02-064648 A1 | 8/2002 |
| WO | 02-065212 A1 | 8/2002 |

OTHER PUBLICATIONS

Crawford et al., M. K., "New Materials for 157 nm Photoresists: Characterization and Properties", *Proceedings of SPIE*, vol. 3999, pp. 357 to 364 (2000).
Kodama et al., S., "Synthesis of Novel Fluoropolymer for 157 nm Photoresists by Cyclo-polymerization", *Proceedings of SPIE*, vol. 4690, pp. 76 to 83 (2000).
Notice of Reasons for Rejection mailed Feb. 17, 2009, in corresponding Japanese Patent Application No. 2003-391139, with partial English language translation.

* cited by examiner

*Primary Examiner*—Cynthia H Kelly
*Assistant Examiner*—Anca Eoff
(74) *Attorney, Agent, or Firm*—Wenderoth, Lind & Ponack, LLP.

(57) ABSTRACT

A high-molecular compound and a low-molecular compound or both having an alkali-soluble site (i) wherein at least a part of the alkali-soluble site (i) is protected with (ii) a halogen atom-containing acetal type acid-dissociative, dissolution inhibiting group, as well as a photoresist composition comprising the same. The photoresist composition is highly stable during storage and can give a resist pattern excellent in sectional rectangular shape and having high transparency to an exposure light, particularly a light having a wavelength of 300 nm or less.

6 Claims, No Drawings

PHOTORESIST COMPOSITION, AND LOW-MOLECULAR COMPOUND AND HIGH-MOLECULAR COMPOUND FOR THE PHOTORESIST COMPOSITION

TECHNICAL FIELD

The present invention relates to a photoresist composition used in patterning of a semiconductor integrated circuit by lithography, a low-molecular compound and a high-molecular compound preferable for constituting the photoresist composition, and in particular to a photoresist composition excellent in transparency in fine patterning with a light source having a wavelength of 300 nm or less, especially a KrF, ArF, or $F_2$ excimer laser, particularly the $F_2$ excimer laser, and to a low-molecular compound and a high-molecular compound preferable for constituting the photoresist composition.

BACKGROUND ART

Fine patterning of semiconductor integrated circuits has been achieved by progress in photolithography and its related technologies. As is well known, this photolithography is supported mainly by two technologies. One technology is related to the exposure light wavelength and numerical aperture of a miniaturized projection light exposure device called a stepper or a scanner, and the other is concerned with resist characteristics composed chiefly of transfer resolution of a photoresist composition onto which a mask pattern is to be transferred by the miniaturized projection light exposure device. By the combined actions of the two technologies, the processing accuracy of a semiconductor integrated circuit pattern by photolithography has been improved.

The wavelength of a light source used in the miniaturized projection light exposure device becomes shorter and shorter in accepting a demand for higher resolution of circuit patterns. Generally, g-line of 436 nm in a main spectrum of a mercury lamp is used for a resist resolution of about 0.5 μm; i-line of 365 nm in a main spectrum of the mercury lamp is used for a resolution of about 0.5 to 0.30 am; a KrF excimer laser light of 248 nm is used for a resolution of about 0.30 to 0.15 μm; an ArF excimer laser light of 193 nm is used for a resolution of about 0.15 μm or less; and use of an $F_2$ excimer laser light of 157 nm, an $Ar_2$ excimer laser light of 126 nm, and an EUV (extreme ultraviolet, wavelength 13 nm) light is examined for further fine patterning.

In view of the photoresist composition, on one hand, a combination thereof with an organic or inorganic anti-reflective coating film or a lighting system has been devised, and in lithography using a KrF excimer laser light, the life of a photoresist for KrF is prolonged, and a photoresist composition in consideration with about 110 nm of below λ/2 is under development. In lithography using an ArF excimer laser light, it is desired to provide photoresist compositions for ArF preferable for mass production in the future of those for a node of about 90 nm or less. Lithography using the $F_2$ excimer laser attracts attention as technology taking responsibility for fine processing at 65 nm or less in the future, and a photoresist composition which can be applied satisfactorily to lithography using the $F_2$ excimer laser is being developed.

As is well known in lithography, a photoresist layer applied on a laminate semiconductor substrate is irradiated with a short-wavelength light (light exposure) via a mask reflecting a negative or positive pattern of a semiconductor integrated circuit pattern to be realized. The photoresist composition contains, as a main component, a photosensitive polymer which upon reacting with the irradiation light, will be rendered insoluble (negative) or soluble (positive) with an alkali, and after exposure to the patterning light, is subjected to heat (post exposure bake, also referred to as "PEB") for securing the reaction of the resist layer by light exposure, and then subjected to development to remove soluble parts, whereby a photoresist pattern layer accurately reflecting the circuit pattern to be realized is formed on the laminate semiconductor substrate. Thereafter, the patterned photoresist layer may be sufficiently cured by heating (post bake) to make it durable to etching in a next step. In the etching step, the surface layer or the top layer of the laminate semiconductor substrate is subjected to dry-etching along the pattern with the patterned photoresist layer as a mask.

Accordingly, the major properties required for the photoresist composition are to achieve resolution, and the first property for achieving this resolution is "transparency to irradiation light" by which the patterning irradiation light reaches not only the surface of the resist layer but also the bottom at the side of the substrate thereby sufficiently photosensitizing the irradiated portion as a whole in such thickness as to include the bottom. By securing this transparency, it is possible to realize a pattern of high resolution or an excellent pattern having a sectional shape in a rectangular shape having almost the same width from the top to base after patterning development.

To secure this transparency is also important for development of a resist composition coping with a shorter wavelength of irradiation light. For the transparency to exposure light, the development of a base polymer itself is advancing, and several kinds of excellent polymers have been proposed. As promising base polymers, fluorine-containing norbornene polymers (Non-patent document 1 (Proceedings of SPIE, Vol. 3999, (2000) pp357-364)), polymers in Patent document 1 (International publication WO 00/67072 Pamphlet) and Patent document 5 (Japanese Patent Application Laid-open No. 2002-333715), fluorine-containing monocyclic polymers (Patent document 2 (Japanese Patent Application Laid-open No. 2002-90997)), and polymers in Patent document 3 (International publication WO 02/64648 Pamphlet), Patent document 4 (International publication WO 02/65212 Pamphlet), and Non-patent document 2 (Shun-ichi Kodama, et al., "Synthesis of Novel Fluoropolymer for 157 nm Photoresists by Cyclo-polymerization" Proceedings of SPIE, Vol. 4690, (2000) pp76-83) have been reported.

These polymers, as can be confirmed or estimated from descriptions in these documents, are determined to be capable of securing transparency at the practical level to a light having a wavelength of 300 nm or less.

DISCLOSURE OF INVENTION

The above-described polymer improves transparency by introducing a fluorine atom into a main chain or a side chain of its base resin. The acid-dissociative, dissolution inhibiting group (hereinafter referred to sometimes as a protective group) includes halogen atom-free groups, for example a tertiary alkyl ester type acid-dissociative, dissolution inhibiting group such as a general tert-butyl ester group, an ether-based, acid-dissociative dissolution inhibiting group such as a tert-butyl ether group, and an acetal type acid-dissociative, dissolution inhibiting group such as a tetrahydropyranyl ether group or a 1-ethoxyethoxy group.

However, these dissolution inhibiting groups, particularly a carbonyl group of an ester, have absorption at 157 nm and are thus poor in transparency. An ether and acetate, though not having such absorption, are still desired to improve transparency.

The present invention has been achieved in view of these circumstances, and the object of the invention is to provide a photoresist composition excellent in resolution and having high transparency to an exposure light, particularly a light having a wavelength of 300 nm or less and a low-molecular compound and a high-molecular compound for obtaining the photoresist composition.

To solve the problems, the present inventors made extensive study, and as a result, they found:

(1) To obtain transparency in the photoresist composition particularly to an ArF or $F_2$ excimer laser light, the introduction of fluorine atoms into its base resin component is effective, and the introduction of fluorine atoms into a main chain or a side chain of polymerizable units of the base resin is proposed as shown in the above-described polymer. However, when fluorine atoms are to be introduced into a main chain or a side chain of the resin, there is a limit to the amount of fluorine atoms which can be easily introduced, and for increasing the amount of fluorine atoms introduced, further complicated reaction is necessary. For controlling the alkali solubility of the base resin component, a fluorine atom can be introduced into an acid-dissociative, dissolution inhibiting group (protective group) modified by its soluble terminal site thereby easily introducing the fluorine atom into the base resin to further improve the transparency of the resin component to an exposure light.

(2) The protective group, owing to its role, will be eliminated from the base resin component in a step of exposing the resist to light. As a result, the fluorine atom in the protective group does not remain in the base resin component, but this is not problematic because it is enough for the transparency of the resin achieved by fluorine atoms to be maintained until light exposure is completed. The physical and chemical properties of the resin may be influenced when a large amount of fluorine atoms are contained in the resin, and thus the system wherein fluorine atoms introduced in excess for merely achieving transparency are removed after light exposure would rather be considered desirable.

The present invention has been achieved on the basis of such finding. That is, the photoresist composition of the present invention comprises: (A) a base resin component having alkali-solubility changed by the action of an acid; and (B) an acid generator, wherein the base resin component (A) comprises a compound having an alkali-soluble site (i), at least a part of the alkali-soluble site (i) is protected with (ii) a halogen atom-containing acetal type dissolution inhibiting group, and the dissolution inhibiting group (ii) is a group dissociable from the alkali-soluble site (i) by an acid.

The low-molecular compound for photoresist according to the present invention is a low-molecular compound for an acid-dissociative, dissolution inhibiting agent contained in a photoresist composition generating an acid by light exposure and changing solubility in an alkaline solution by the action of the acid to form a pattern, wherein the low-molecular compound has an alkali-soluble site (i), at least a part of the alkali-soluble site (i) is protected with (ii) a halogen atom-containing acetal type dissolution inhibiting group, and the dissolution inhibiting group (ii) is a group dissociable from the alkali-soluble site (i) by an acid.

The high-molecular compound for photoresist according to the present invention is a high-molecular compound for a base resin component constituting a photoresist composition generating an acid by light exposure and changing alkali-solubility by the action of the acid to form a pattern, wherein the high-molecular compound has an alkali-soluble site (i), at least a part of the alkali-soluble site (i) is protected with (ii) a halogen atom-containing acetal type dissolution inhibiting group, and the dissolution inhibiting group (ii) is a group dissociable from the alkali-soluble site (i) by an acid.

In the present invention, the low-molecular compound, the high-molecular compound, and the resin composition comprising at least one kind of these compounds can achieve the following excellent effects.

In the present invention, the high-molecular compound has a weight-average molecular weight of 3000 to 80000, preferably 5000 to 50000.

In the present invention, the low-molecular compound has a weight-average molecular weight of 500 to 3000, preferably 1000 to 3000.

That is, when a fluorine atom is used as a halogen atom in a protective group in the present invention, the fluorine atom can, without relying on complex reaction, be introduced easily into a base resin component of the photoresist composition, to further improve the transparency of the resin component to a light having a wavelength of 300 nm or less. Particularly, the resist composition, as compared with a conventional resist composition free of halogen in its protective group, can achieve a significant improvement in transparency to an exposure light particularly using an $F_2$ excimer laser.

It is considered that the elimination of the protective group in the present invention is suppressed because the group contains an electron attractive halogen. By using this protective group whose elimination is suppressed, the light sensitivity in the vicinity of the surface of the resist layer can be near to the light sensitivity of a deep part of the resist layer, and as a result, easy resolution of a line and space resist pattern having a narrow space between lines can be expected.

In addition, the following effects can also be expected:

(1) The halogen atom-containing acetal type acid-dissociative, dissolution inhibiting group used in the present invention has higher transparency than that of the halogen-containing ester type acid-dissociative, dissolution inhibiting group, and can thus realize higher transparency than by the conventional material.

(2) The storage stability of the photoresist composition can be improved because the elimination of the protective group can be suppressed by incorporation of the halogen.

(3) A bromine atom can be used as the halogen in the protective group to improve the light sensitivity of a resist composition for exposure to an electron beam or X-ray as a light source.

(4) Allowance in establishing regulatory factors such as depth of focus in the light exposure process can be increased.

(5) The resistance to etching of a resist film can be improved due to the presence of the halogen atom.

(6) A cyclic group can be introduced into the protective group. In this case, the cyclic group can have a double bond, and this double bond can be utilized to introduce a hydroxyl group via an epoxy group to improve the hydrophilicity of the resist composition and the adhesion thereof to a substrate.

BEST MODE(S) FOR CARRYING OUT THE INVENTION

As described above, the present invention is characterized in that any one of a high-molecular compound and a low-molecular compound or both having an alkali-soluble site (i), wherein at least a part of the alkali-soluble site (i) is protected with (ii) a halogen atom-containing acetal type acid-dissociative, dissolution inhibiting group, is used as a constituent element of the photoresist composition.

In such constitution, the alkali-soluble site (i) is known as exemplified by the above non-patent documents and patent documents or from the previously proposed KrF resist, ArF resist and F$_2$ resist. Such an alkali-soluble site includes, but is not limited to, an alcoholic hydroxyl group, a phenolic hydroxyl group, and a carboxyl group. In the present invention, the alkali-soluble site is desirably at least one member selected from an alcoholic hydroxyl group, a phenolic hydroxyl group, and a hydroxyl group of a carboxyl group. Especially, an alcoholic hydroxyl group or a fluorine-containing alcoholic hydroxyl group is preferable because of its high transparency and suitable alkali solubility.

The halogen atom-containing acetal type acid-dissociative, dissolution inhibiting group (ii) is desirably a group represented by the following general formula (1):

$$—O—C(R^1)(R^2)—O—R^3 \quad (1)$$

wherein $R^1$ and $R^2$ independently represent a hydrogen atom or a lower alkyl group, and $R^3$ represents a halogen-containing substituted or unsubstituted hydrocarbon group.

A substituent group may or may not be present in the constitution, and the substituent group when present is preferably a polar group such as a hydroxyl group or lactone group in order to increase affinity for a resist solvent, increase affinity for an alkali developing solution, and achieve excellent adhesion to a substrate. For F$_2$ excimer laser light, a hydroxyl group is particularly preferable because it has excellent transparency.

The hydrocarbon group includes linear, branched, or cyclic saturated aliphatic or unsaturated aliphatic hydrocarbon groups having 1 to 20 carbon atoms. In particular, 1 to 16 carbon atoms, preferably 1 to 12 carbon atoms of linear, branched, or cyclic saturated aliphatic or unsaturated aliphatic hydrocarbon groups are industrially preferable.

The hydrocarbon carbon group includes a methyl group, ethyl group, n-propyl group, isopropyl group, n-butyl group, isobutyl group, n-pentyl group, cyclopentyl group, methyl cyclopentyl group, ethyl cyclopentyl group, n-hexyl group, cyclohexyl group, methyl cyclohexyl group, ethyl cyclohexyl group, heptyl group, octyl group, nonyl group, decanyl group, dodecanyl group, and groups wherein one hydrogen atom was removed from bicycloalkane, bicyloalkene, tricycloalkane, tetracycloalkane, methyl bicycloalkane, methyl bicycloalkene, methyl tricycloalkane, methyl tetracycloalkane, ethyl bicycloalkane, ethyl bicycloalkene, ethyl tricycloalkane, or ethyl tetracycloalkane.

Specific examples of the cyclic hydrocarbon group include groups wherein one hydrogen atom was removed from adamantane, norbornane, norbornene, methyl norbornane, ethyl norbornane, methyl norbornene, ethyl norbornene, isobornane, tricyclodecane, or tetracyclododecane. Such polycyclic group can be selected from a large number of groups proposed in ArF resist. Among these, an adamantyl group, norbonyl group, norbornenyl group, methyl norbornyl group, ethyl norbornyl group, methyl norbornenyl group, ethyl norbornenyl group, and tetracyclododecanyl group are industrially preferable.

The positions and the number of halogen atoms and the chemical formula are not particularly limited in the above constitution, and one or more halogen atoms or lower perhalogenoalkyl groups such as a trifluoromethyl group, perfluoroethyl group, and perfluorobutyl group may be bonded to the $R^3$.

It is desired for excellent acid dissociation and from an industrial viewpoint that $R^3$ in the general formula (1) is a group represented by the following general formula (2):

$$—[C(R^5)(R^6)]_n—R^4 \quad (2)$$

wherein $R^4$ represents a halogen-containing linear or cyclic hydrocarbon group, $R^5$ and $R^6$ independently represent a hydrogen atom or a lower alkyl group, and n is 0 or an integer of 1 to 3.

Particularly, n is preferably 0 or 1 since the effect of electron attraction of the halogen atom can be easily utilized and the glass transition point of the high-molecular compound having such group is high. Examples of $R^1$, $R^2$, $R^5$, and $R^6$ include a hydrogen atom and lower alkyl groups having carbon atoms of 1 to 5 such as a methyl group, ethyl group, propyl group, isopropyl group, and butyl group. It is particularly preferable that $R^1$, $R^2$, $R^5$, and $R^6$ are simultaneously hydrogen atoms.

For excellent acid dissociation and from an industrial viewpoint, the position to which the halogen atom or the halogenoalkyl group is bonded is desirably the second or third position relative to the carbon atom (carbon atom to which $R^5$ and $R^6$ are bonded) adjacent to $R^4$.

The halogen-containing linear or cyclic hydrocarbon group includes a halogen-containing linear alkyl group, a halogen-containing cyclic alkyl group, and a halogen-containing cyclic alkenyl group. The cyclic alkyl group, linear alkyl group, and alkenyl group may be those mentioned with respect to $R^3$ above. Particularly, a 1-halogen-substituted linear lower alkyl group, a halogen-containing norbornyl group, and a halogen-containing norbornenyl group are more excellent in acid dissociation and industrially suitable. The halogen-containing norbornenyl group has a double bond, and this double bond can be utilized to introduce a hydroxyl group via an epoxy group to improve the hydrophilicity of the resist composition and the adhesion thereof to a substrate.

The halogen includes fluorine, chlorine, bromine, and iodine, among which a fluorine atom can be used to improve transparency to exposure light, while bromine can achieve higher sensitivity, and thus the fluorine or bromine atom is preferable. Especially, the fluorine atom is most preferable.

The acetal type acid-dissociative, dissolution inhibiting group includes a tetrahydropyranyl group, 1-ethoxyethyl group, 1-ethoxymethyl group, methoxymethyl group, methoxyethoxymethyl group, norbornyl methoxymethyl group, and norbornenyl methoxymethyl group. In the present invention, the acetal type acid-dissociative, dissolution inhibiting group into which one or more halogen atoms or haloalkyl groups were introduced is used.

The low-molecular compound preferable as the acid-dissociative, dissolution inhibiting agent contained in the photoresist composition of the present invention includes, for example, low-molecular compounds wherein at least a part of alkali-soluble sites such as an alcoholic hydroxyl group, a phenolic hydroxyl group, and a hydroxyl group of a carboxyl group are protected with the above-mentioned "acetal type acid-dissociative group containing one or more halogen atoms".

Such compounds include, for example, compounds represented by the following general formulae (3) and (4):

-continued

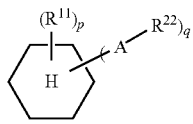

(4)

wherein $R^{11}$ represents a hydrogen atom, an alkyl group, an alkoxyl group, or a fluorine atom, $R^{22}$ represents a halogen atom-containing acetal type acid-dissociative, dissolution inhibiting group, A is —C($C_nF_{2n+1}$)($C_mF_{2m+1}$)—O—CO—, —C($C_nF_{2n+1}$)($C_mF_{2m+1}$)—, or —O—CO—, and each of n, m, p, and q is independently an integer of 1 to 4.

The halogen atom-containing acetal type acid-dissociative, dissolution inhibiting group is the one described above.

Specific examples of the compounds represented by the above general formula include compounds represented by the following chemical formulae (5) to (8):

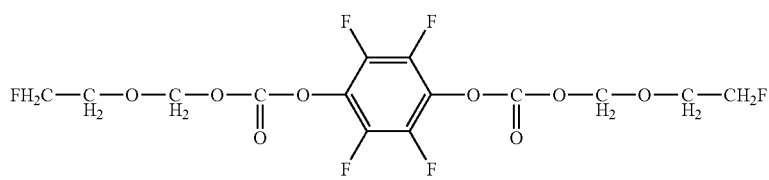

(5)

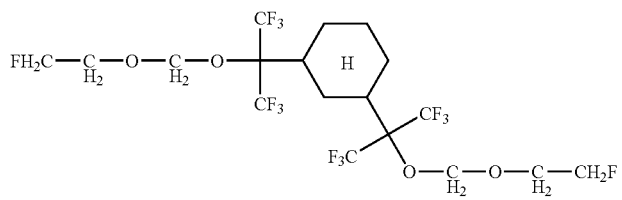

(6)

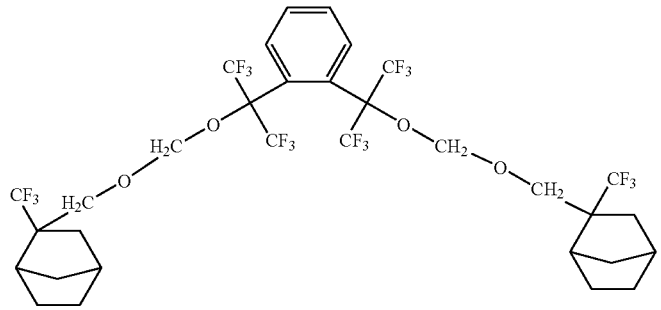

(7)

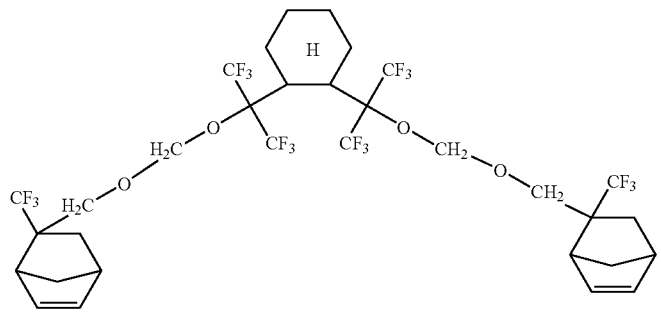

(8)

The low-molecular compound used in the acid-dissociative, dissolution inhibiting agent contained in the photoresist composition, when shown in a state before addition of a protective group, is usefully a compound represented by the following formula 4A:

Formula 4A

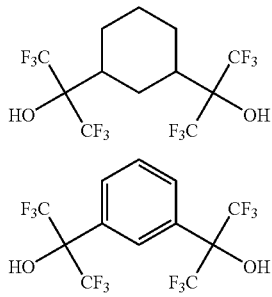

The dissolution inhibiting agent composed of this low-molecular compound can be used to suppress the phenomenon of a reduction in a resist film by an alkali developing solution.

The high-molecular compound (A) as the base resin component is a high-molecular compound composed of the polymerizable units represented by formulae 5A and 6A below, wherein at least a part of alkali-soluble sites is protected with the above-mentioned "acetal type acid-dissociative group containing one or more halogen atoms", or a high-molecular compound composed of the polymerizable units represented by the formulae 5A and 6A and other polymerizable units copolymerizable with said polymerizable units, wherein at least a part of alkali-soluble sites is protected with the above-mentioned "acetal type acid-dissociative group containing one or more halogen atoms".

Formula 5A

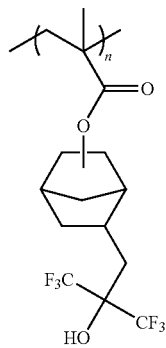 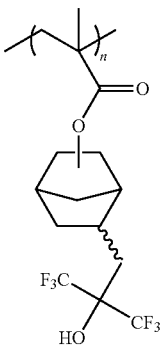

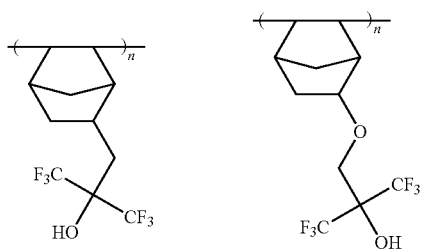

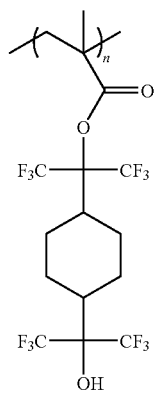

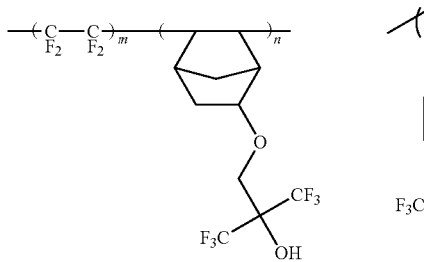 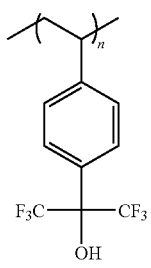

Formula 6A

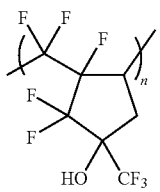

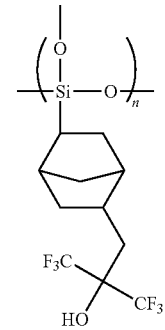

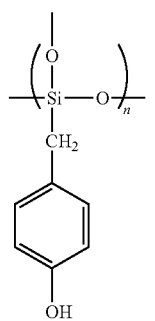

-continued

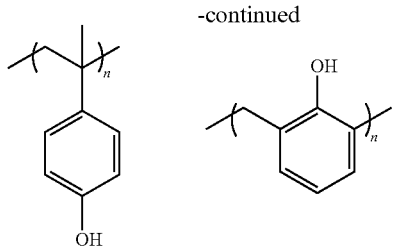

The high-molecular compounds represented by the formulae 5A and 6A above are known. However, the compounds wherein at least a part of alkali soluble groups, that is, a fluorine alcohol, a carboxylic acid, a phenolic hydroxyl group, etc. are replaced by the "halogen atom-containing acetal type acid-dissociative, dissolution inhibiting group" in the present invention are not known.

In the present invention, a polymer comprising alkali-soluble constitutional units (a1) each comprising an alicyclic group having both (i) a fluorine atom or a fluoroalkyl group and (ii) an alcoholic hydroxyl group, wherein at least a part of the alcoholic hydroxyl group is replaced by the halogen atom-containing acetal type acid-dissociative, dissolution inhibiting group and changes alkali-solubility by the action of an acid is preferable because the effect of the part of the protective group in the present invention is significantly excellent to improve transparency.

The polymer (A') before substitution with the "halogen atom-containing acetal type acid-dissociative, dissolution inhibiting group" is known as described in the patent documents 1, 3, and 4 or in the non-patent document 2.

However, the compounds comprising the halogen atom-containing acetal type acid-dissociative, dissolution inhibiting group introduced into the above polymer are novel and not known hitherto. The polymer (A') is not limited insofar as it is a polymer comprising alkali-soluble constitutional units (a1) each comprising an alicyclic group having both (i) a fluorine atom or a fluoroalkyl group and (ii) an alcoholic hydroxyl group, wherein the polymer changes alkali-solubility by the action of an acid.

The phrase "changes alkali-solubility by the action of an acid" refers to a change in a light-exposed portion of the polymer, wherein when the alkali-solubility of the exposed portion is increased, the exposed portion becomes alkali-soluble and hence the resist composition can be used as a positive resist, while when the alkali-solubility of the exposed portion is decreased, the exposed portion becomes alkali-insoluble and hence the resist composition can be used as a negative resist.

The alkali-soluble constitutional units (a1) each comprising an alicyclic group having both (i) a fluorine atom or a fluoroalkyl group and (ii) an alcoholic hydroxyl group may be constitutional units with an organic group having both the groups (i) and (ii) bonded to the alicyclic group therein.

The alicyclic group can be exemplified by groups wherein one or more hydrogen atoms were removed from a monocyclic or polycyclic hydrocarbon such as cyclopentane, cyclohexane, bicycloalkane, tricycloalkane, or tetracycloalkane.

Specific examples of the polycyclic hydrocarbon include groups wherein one or more hydrogen atoms were removed from polycycloalkane such as adamantane, norbornane, isobornane, tricyclodecane, or tetracyclododecane.

Among these groups, groups derived from cyclopentane, cyclohexane, or norbornane by removing hydrogen atom(s) are industrially preferable.

Examples of the fluorine atom or fluoroalkyl group (i) include a fluorine atom and lower alkyl groups having part or all of their hydrogen atoms replaced by fluorine atom(s). Specific examples include a trifluoromethyl group, a pentafluoroethyl group, a heptafluoropropyl group, and a nonafluorobutyl group, among which a fluorine atom and a trifluoromethyl group are industrially preferable.

The alcoholic hydroxyl group (ii) may be either a single hydroxyl group or an alcoholic hydroxyl group-containing alkyloxy group, an alcoholic hydroxyl group-containing alkyloxyalkyl group, or an alcoholic hydroxyl group-containing alkyl group, such as an alkyloxy group, alkyloxyalkyl group, or alkyl group having a hydroxyl group. Examples of the alkyloxy group, alkyloxyalkyl group, or alkyl group include lower alkyloxy groups, lower-alkyloxy-lower-alkyl groups, and lower alkyl groups.

Specific examples of the lower alkyloxy groups include a methyloxy group, an ethyloxy group, a propyloxy group, and a butyloxy group; specific examples of the lower-alkyloxy-lower-alkyl groups include a methyloxymethyl group, an ethyloxymethyl group, a propyloxymethyl group, and a butyloxymethyl group; and specific examples of the lower alkyl groups include a methyl group, an ethyl group, a propyl group, and a butyl group.

In the alcoholic hydroxyl group-containing alkyloxy group, alcoholic hydroxyl group-containing alkyloxyalkyl group, or alcoholic hydroxyl group-containing alkyl group (ii), the alkyloxy group, alkyloxyalkyl group, or alkyl group may have part or all of its hydrogen atoms replaced by fluorine atom(s). It is preferred that the alcoholic hydroxyl group-containing alkyloxy group or the alcoholic hydroxyl group-containing alkyloxyalkyl group has part of the hydrogen atoms in its alkyloxy moiety replaced by fluorine atom(s), or the alcoholic hydroxyl group-containing alkyl group has part of the hydrogen atoms in the alkyl moiety replaced by fluorine atom(s), that is, preferred examples include an alcoholic hydroxyl group-containing fluoroalkyloxy group, an alcoholic hydroxyl group-containing fluoroalkyloxyalkyl group, and an alcoholic hydroxyl group-containing fluoroalkyl group.

Examples of the alcoholic hydroxyl group-containing fluoroalkyloxy groups include a $(HO)C(CF_3)_2CH_2O-$ group, a 2-bis(trifluoromethyl)-2-hydroxy-ethyloxy group, a $(HO)C(CF_3)_2CH_2CH_2O-$ group, and a 3-bis(trifluoromethyl)-3 hydroxypropyloxy group; examples of the alcoholic hydroxyl group-containing fluoroalkyloxyalkyl groups include a $(HO)C(CF_3)_2CH_2O-CH_2-$ group and a $(HO)C(CF_3)_2CH_2CH_2O-CH_2-$ group; and examples of the alcoholic hydroxyl group-containing fluoroalkyl groups include a $(HO)C(CF_3)_2CH_2-$ group, a 2-bis(trifluoromethyl)-2 hydroxy-ethyl group, a $(HO)C(CF_3)_2CH_2CH_2-$ group, and a 3-bis(trifluoromethyl)-3-hydroxypropyl group.

The groups (i) and (ii) may be directly bonded to the alicyclic group. Because of excellency in transparency, in alkali-solubility, and in resistance to dry etching, and easy industrial availability, the constitutional unit (a1) is particularly preferably an unit represented by the general formula (9) below, which is formed by cleaving a double bond of norbornene ring to which the alcoholic hydroxyl group-containing fluoroalkyloxy group, the alcoholic hydroxyl group-containing fluoroalkyloxyalkyl group, or the alcoholic hydroxyl group-containing fluoroalkyl group is bonded.

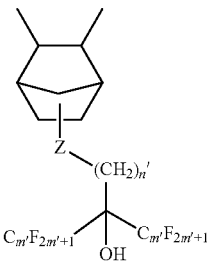

(9)

wherein Z represents an oxygen atom, an oxymethylene group (—O(CH$_2$)—), or a single bond, and n' and m' independently represent an integer of 1 to 5.

Polymer units used in combination with the unit (a1) are not particularly limited, and those conventionally known can be used. When the resin composition is used as a positive-working polymer (A'-1) having alkali-solubility increased by the action of an acid, the constitutional unit (a2) derived from a known (meth)acrylic ester having an acid-dissociative, dissolution inhibiting group is preferred because of excellent resolution.

Examples of the constitutional unit (a2) include constitutional units derived from a tertiary alkyl ester of (meth)acrylic acid, such as tert-butyl (meth)acrylate or tert-amyl (meth)acrylate.

The polymer (A') may be a polymer (A'-2) having alkali-solubility increased by the action of an acid and further comprising a fluoroalkylene constitutional unit (a3) for improving the transparency of the polymer. By incorporation of the constitutional unit (a3), the transparency of the polymer is further improved. The constitutional unit (a3) is preferably a unit derived from tetrafluoroethylene.

The general formulae (10) and (11) representing the polymers (A'-1) and (A'-2) respectively are shown below.

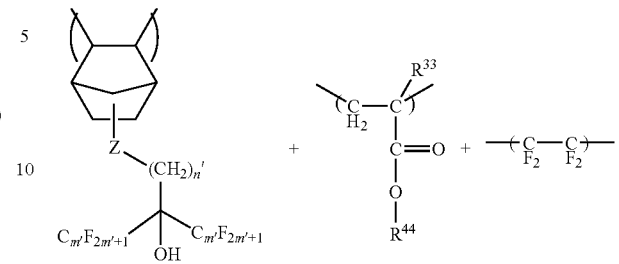

(10)

wherein Z, n', and m' are as defined in the general formula (9), R$^{33}$ represents a hydrogen atom or a methyl group, and R$^{44}$ represents an acid-dissociative, dissolution inhibiting group.

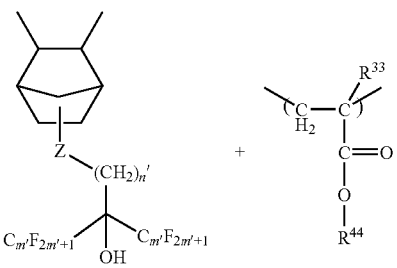

(11)

wherein Z, n', m', R$^{33}$, and R$^{44}$ are as defined in the general formula (10).

The polymer (A'-1) and (A'-2) containing the general formula (8) have different structural formulae, and may have the following constitutional unit falling under the concept of the polymer having alkali-solubility changed by the action of an acid, comprising the alkali-soluble constitutional unit (a1) containing an alicyclic group having both (i) a fluorine atom or a fluoroalkyl group and (ii) an alcoholic hydroxyl group.

That is, in the constitutional unit (a1), the fluorine atom or fluoroalkyl group (i) and the alcoholic hydroxyl group (ii) are bonded respectively to the alicyclic group constituting a main chain.

The fluorine atom or fluoroalkyl group (i) includes those described above. The alcoholic hydroxyl group (ii) is a single hydroxyl group.

The polymer (A') having such units is described in the patent document 3 or 4 or the non-patent document 4, and is formed by cyclopolymerization of a diene compound having a hydroxyl group and a fluorine atom. The diene compound is preferably heptadiene easily forming a polymer having a 5- or 6-membered ring excellent in transparency and resistance to dry etching, and the most preferable in industry is a polymer formed by cyclopolymerization of 1,1,2,3,3-pentafluoro-4-trifluoromethyl-4-hydroxy-1,6-heptadiene (CF$_2$=CFCF$_2$C(CF$_3$)(OH)CH$_2$CH=CH$_2$).

When the resin composition is used as a positive-working polymer (A'-3) having alkali-solubility increased by the action of an acid, a hydrogen atom of its alcoholic hydroxyl group should be replaced by the "halogen atom-containing acetal type acid-dissociative, dissolution inhibiting group".

The halogen atom-containing acetal type acid-dissociative,dissolution inhibiting group includes those described above.

The degree of replacement of all hydroxyl groups thereby is in the range of 10 to 60%, preferably 14 to 55%, in order to achieve excellent pattern formability, adhesiveness, and resolution.

The general formula (12) representing the polymer (A'-3) is shown below:

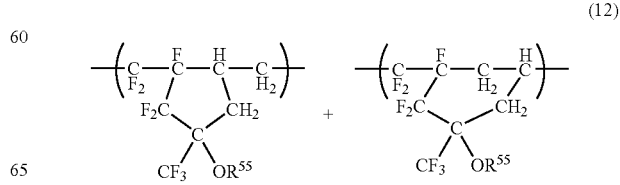

(12)

wherein $R^{55}$ represents a hydrogen atom or a halogen atom-containing acetal type acid-dissociative, dissolution inhibiting group, and each of x and y is 10 to 50 mol %.

The polymer (A') can be synthesized by a known method, for example, a method described in the patent document 1, 3, or 4 or the non-patent document 2. The polystyrene-equivalent, weight-average molecular weight of the resin in the component (A), as determined by GPC, is not particularly limited, but is preferably 5000 to 80000, more preferably 8000 to 50000. The degree of dispersion (Mw/Mn) is about 1.0 to 5.0, preferably 2.5 or less.

The polymer (A) may be comprised of one or more kinds of resins, for example, a mixture of two or more resins selected from the (A'-1), (A'-2), and (A'-3) whose hydrogen atoms are replaced by halogen atom-containing acetal type acid-dissociative, dissolution inhibiting groups, and may further contain another resin conventionally known for photoresist composition.

The method of introducing the above-described protective group is described. The compound represented by the following formula 11A can be deprotected by an acid.

Formula 11A

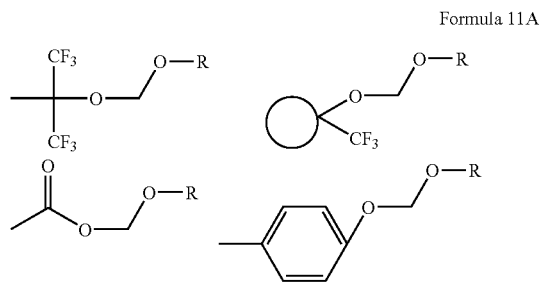

The compound represented by the formula 11A above can be obtained by reacting the chloromethyl ether compound obtained by the reaction in the formula 12A, with a compound represented by the following formula 13A.

Formula 12A

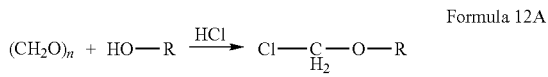

Formula 13A

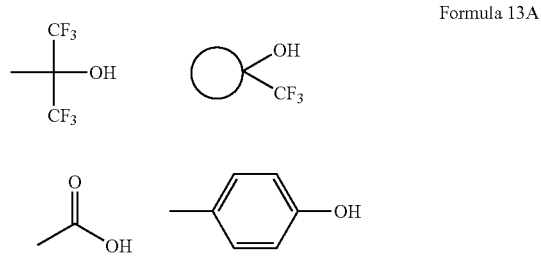

In the present invention, a halogen atom-containing alcohol compound is used as a starting material to synthesize the corresponding chloromethyl ether derivative which is then reacted with a low-molecular or high-molecular compound having an alkali-soluble group to give the objective compound. The compound can be used in a resist material to realize the dissolution inhibition thereof in an alkali developing solution before light exposure and exhibition of alkali solubility with de-protection (in the case of a positive resist) in a post-exposure heating step.

The acid generator (B) used in the photoresist composition of the present invention can be selected suitably from arbitrary compounds generating an acid upon irradiation with radiation rays. Various acid generators have been proposed, and especially preferred are onium salts such as diphenyliodonium trifluoromethanesulfonate, (4-methoxyphenyl)phenyliodonium trifluoromethanesulfonate, bis(p-tert-butylphenyl)iodonium trifluoromethanesulfonate, triphenylsulfonium trifluoromethanesulfonate, (4-methoxyphenyl)diphenylsulfonium trifluoromethanesulfonate, (4-methylphenyl)diphenylsulfonium nonafluorobutanesulfonate, (p-tert-butylphenyl)diphenylsulfonium trifluoromethanesulfonate, diphenyliodonium nonafluorobutanesulfonate, bis(p-tert-butylphenyl)iodonium nonafluorobutanesulfonate, and triphenylsulfonium nonafluorobutanesulfonate (TPS-PFBS). Among these, preferred are sulfonium salts comprising a fluoroalkylsulfonic acid ion as anion since they have appropriate acid strength and diffusion properties in the resist film. The acid generators may be used singly or as a mixture of two or more thereof. The amount of the acid generator incorporated is for example 0.5 to 30 parts by weight relative to 100 parts by weight of the resin component. When the amount is smaller than this range, the formation of a latent image may be unsatisfactory, and when the amount is larger, the resistant resist composition may be poor in storage stability.

Next, the nitrogen-containing compound (C) added if necessary to the resist composition of the second aspect of the present invention is described.

(Nitrogen-Containing Compound (C))

It has been known that a nitrogen-containing compound is incorporated in a small amount as an acid diffusion-preventing agent into the chemically amplified resist composition. In the present invention, such a known nitrogen-containing compound can be added. Examples of the nitrogen-containing compounds include amines and ammonium salts.

Examples of the amines include aliphatic secondary amines such as diethylamine, dipropylamine, dibutylamine, and dipentylamine; aliphatic tertiary amines such as trimethylamine, triethylamine, tripropylamine, tributylamine, tripentylamine, N,N-dimethylpropylamine, N-ethyl-N-methylbutylamine, trihexylamine, triheptylamine, trioctylamine, tridecanylamine, tridodecylamine, and tritetradecanylamine, wherein the three alkyl groups bonded to nitrogen in the trialkylamines may be the same or different; tertiary alkanolamines such as N,N-dimethylmonoethanolamine, triisopropanolamine, N,N-diethylmonoethanolamine, triethanolamine, and tributanolamine; and aromatic tertiary amines such as N,N-dimethylaniline, N,N-diethylaniline, N-ethyl-N-methylaniline, N,N-dimethyltoluidine, N-methyldiphenylamine, N-ethyldiphenylamine, and triphenylamine.

Examples of the ammonium salts include salts of quaternary alkylammonium ion such as ammonium ion, tetramethylammonium ion, tetraethylammonium ion, tetrapropylammonium ion, tetrabutylammonium ion, or tetrapentylammonium ion, and ion of an organic carboxylic acid having a hydroxyl group, such as lactic acid.

Among these, lower tertiary alkanolamines such as triethanolamine, triisopropanolamine, and tributanolamine, and trialkylamines having 6 to 15 carbon atoms, such as trihexylamine, triheptylamine, trioctylamine, tridecanylamine, tridodecylamine, and tritetradecanylamine are preferable to achieve an excellent effect of suppressing the reduction in a film on the top of a fine resist pattern.

The nitrogen-containing compound (C) is used usually in the range of 0.01 to 2 parts by weight relative to 100 parts by weight of the polymer component (A). When the amount of the compound (C) is smaller than this range, it is not possible to achieve an effect of improving the shape of a pattern by the effect of preventing the diffusion of an acid generated upon exposure to light, while when the amount is too large, the diffusion of an acid is significantly suppressed to deteriorate exposure sensitivity disadvantageously.

In the present invention, an organic carboxylic acid, an oxo-acid of phosphorus, or a derivative thereof can be further contained as an arbitrary component for the purpose of preventing the deterioration in sensitivity caused by adding the nitrogen-containing component (C).

As the organic carboxylic acid, for example, malonic acid, citric acid, malic acid, succinic acid, benzoic acid, or salicylic acid is preferred.

Examples of the oxo-acids of phosphorus and derivatives thereof include phosphoric acid and derivatives thereof, for example, esters such as di-n-butyl phosphate, and diphenyl phosphate; phosphonic acid and derivatives thereof such as esters, for example, dimethyl phosphonate, di-n-butyl phosphonate, phenylphosphonic acid, diphenyl phosphonate, and dibenzyl phosphonate; and phosphinic acid and derivatives thereof such as esters, for example, phosphinic acid and phenylphosphinic acid, among which phosphonic acid is preferable. The organic carboxylic acid, oxo-acid of phosphorus, or derivative component is used in an amount of 0.01 to 5.0 parts by weight relative to 100 parts by weight of the resin component (A).

The resist composition in the second aspect of the present invention is used in the form of a uniform solution obtained by dissolving the resin component (A), the acid generator (B), the nitrogen-containing component (C), and an arbitrary component further added if necessary, in an organic solvent. Specific examples of the organic solvent include ketones such as acetone, methyl ethyl ketone, cyclohexanone, methyl isoamyl ketone, and 2-heptanone; polyhydric alcohols and derivatives thereof, such as monomethyl ether, monoethyl ether, monopropyl ether, monobutyl ether, or monophenyl ether of ethylene glycol, ethylene glycol monoacetate, diethylene glycol, diethylene glycol monoacetate, propylene glycol, propylene glycol monoacetate, dipropylene glycol, or dipropylene glycol monoacetate; cyclic ethers such as dioxane; and esters such as methyl lactate, ethyl lactate, methyl acetate, ethyl acetate, butyl acetate, methyl pyruvate, ethyl pyruvate, methyl methoxypropionate, and ethyl ethoxypropionate. These organic solvents may be used singly or as a mixed solvent of two or more thereof. Especially preferred are propylene glycol monomethyl ether acetate (PGMEA) and ethyl lactate (EL).

The amount of the organic solvent is adjusted so that the resist composition can have a concentration applicable to a substrate or the like to form a resist film.

An additive miscible with the composition, for example, a known dissolution inhibiting agent, an additional resin for improving the performance of the resist film, or a surfactant, a plasticizer, a stabilizer, a coloring agent, or a halation preventing agent for improving the coating properties can be further added if necessary to the resist composition of the present invention.

The resist composition of the present invention is used in a conventional lithographic process to form a resist pattern. In this process, the photoresist composition is applied by rotational coating onto a substrate and dried to form a resist film. The resist film is then exposed selectively via a mask pattern and then subjected to post-exposure heating. Finally, the resist film can be developed with an aqueous alkali solution to form a resist pattern. Further, post bake treatment may be conducted if necessary. The light source is not limited, and far ultraviolet light, specifically an electron beam, a soft X-ray, or an X-ray such as an ArF excimer laser, an $F_2$ excimer laser, an EUV (extreme ultraviolet) light, etc. can be used. Particularly, the $F_2$ excimer laser is preferable.

The conditions, that is, the number of revolutions of the resist coating, the prebake temperature, the exposure conditions, the post exposure bake conditions, and the alkaline development conditions may be those conventionally used. Specifically, the number of revolutions is about 2000 rpm, specifically about 1200 to 3500 rpm, and the prebake temperature is in the range of 70 to 130° C., thus forming a resist film having a thickness of 80 to 250 nm. Exposure may be conducted through a mask. As a mask in the selective exposure, a general binary mask is used. As the mask, a phase-shifting mask may be used. The post exposure bake temperature is in the range of from 90 to 140° C., and alkali development conditions are such that development is conducted using 1 to 5 wt % TMAH (tetramethylammonium hydroxide) developer solution at 23° C. for 15 to 90 seconds, followed by rinsing with water.

EXAMPLES

Examples of the present invention will be explained below. Note that the Examples merely exemplify the invention preferably, and do not limit it.

(Synthesis of Chloromethyl Ether Compounds)

The method of synthesizing 1-monochloromethoxy-2-monofluoroethane (compound 1), 2-(chloromethoxymethyl)-2-trifluoromethyl norbornane (compound 2), 2-(chloromethoxymethyl)-2-trifluoromethyl norbornene (compound 3) is described in more detail.

Paraformaldehyde was added to 1 equivalent of 2-monofluoroethanol or 2-(trifluoromethyl)bicycle[2,2,1]heptane-2-methanol, or 2-(trifluoromethyl) bicycle[2,2,1]heptene-2-methanol, and 3 equivalents of hydrogen chloride gas were blown into it, and the mixture was reacted at 40 to 100° C. After the reaction was finished, the product was distilled away under reduced pressure to give compounds 1 to 3.

(Introduction of the Chloromethyl Ether Compound into a High-Molecular Compound)

The chloromethyl ether compounds were introduced into resins 1 and 2 described below synthesized by radical polymerization and addition polymerization, to give resins 3 to 12 described below.

Resin Synthesis Example 1

10.0 g of resin 1 (weight–average molecular weight=7500, degree of dispersion (Mw/Mn)=1.74) was dissolved in 100 mL of tetrahydrofuran, and 0.32 g of sodium hydride was added thereto. The mixture was stirred at room temperature until the solution became uniform, and then 0.83 g of the above compound 1 was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L of n-heptane. The precipitated resin was separated by filtration and dried under reduced pressure to give white powder resin. The yield was 7.4 g. This resin is referred to as resin 3. The resin 3 had a weight-average molecular weight of 7800, a degree of dispersion (Mw/Mn) of 1.82, and a protection degree of 19%.

Resin Synthesis Example 2

10.0 g of the above resin 1 was dissolved in 100 mL of tetrahydrofuran, and 0.64 g of sodium hydride was added thereto. The mixture was stirred at room temperature until the solution became uniform, and then 1.66 g of the above compound 1 was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L n-heptane. The precipitated resin was separated by filtration and dried under reduced pressure to give white powder resin. The yield was 9.3 g. This resin is referred to as resin 4. The resin 4 had a weight-average molecular weight of 7700, a degree of dispersion (Mw/Mn) of 1.97, and a protection degree of 38%.

Resin Synthesis Example 3

10.0 g of the above resin 1 was dissolved in 100 mL of tetrahydrofuran, and 0.96 g of sodium hydride was added thereto. The mixture was stirred at room temperature until the solution became uniform, and then 2.49 g of the above compound 1 was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L of n-heptane. The precipitated resin was separated by filtration and dried under reduced pressure to give white powder resin. The yield was 9.3 g. This resin is referred to as resin 5. The resin 5 had a weight-average molecular weight of 7400, a degree of dispersion (Mw/Mn) of 2.02, and a protection degree of 56%.

Resin Synthesis Example 4

10.0 g of the above resin 1 was dissolved in 100 mL of tetrahydrofuran, and 0.32 g of sodium hydride was added thereto. The mixture was stirred at room temperature until the solution became uniform, and then 1.74 g of the above compound 2 was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L of n-heptane. The precipitated resin was separated by filtration and dried under reduced pressure to give white powder resin. The yield was 8.6 g. This resin is referred to as resin 6. The resin 6 had a weight-average molecular weight of 8700, a degree of dispersion (Mw/Mn) of 1.72, and a protection degree of 18%.

Resin Synthesis Example 5

10.0 g of the above resin 1 was dissolved in 100 mL of tetrahydrofuran, and 0.64 g of sodium hydride was added thereto. The mixture was stirred at room temperature until the solution became uniform, and then 3.48 g of the above compound 2 was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L of n-heptane. The precipitated resin was separated by filtration and dried under reduced pressure to give white powder resin. The yield was 9.5 g. This resin is referred to as resin 7. The resin 7 had a weight-average molecular weight of 10800, a degree of dispersion (Mw/Mn) of 1.82, and a protection degree of 37%.

Resin Synthesis Example 6

10.0 g of the above resin 1 was dissolved in 100 mL of tetrahydrofuran, and 0.96 g of sodium hydride was added thereto. The mixture was stirred at room temperature until the solution became uniform, and then 5.22 g of the above compound 2 was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L of n-heptane. The precipitated resin was separated by filtration and dried under reduced pressure to give white powder resin. The yield was 10.5 g. This resin is referred to as resin 8. The resin 8 had a weight-average molecular weight of 9300, a degree of dispersion (Mw/Mn) of 1.85, and a protection degree of 53%.

Resin Synthesis Example 7

10.0 g of the above resin 2 (weight-average molecular weight=27600, degree of dispersion (Mw/Mn)=2.41) was dissolved in 100 mL of tetrahydrofuran, and 0.24 g of sodium hydride was added thereto. The mixture was stirred at room temperature until the solution became uniform, and then 1.35 g of the above compound 2 was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L of n-heptane. The precipitated resin was separated by filtration and dried under reduced pressure to give white powder resin. The yield was 9.0 g. This resin is referred to as resin 9. The resin 9 had a weight-average molecular weight of 30800, a degree of dispersion (Mw/Mn) of 2.15, and a protection degree of 14%.

Resin Synthesis Example 8

10.0 g of the above resin 1 was dissolved in 100 mL of tetrahydrofuran, and 0.32 g of sodium hydride was added thereto. The mixture was stirred at room temperature until the solution became uniform, and then 1.73 g of the compound 3 was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L of n-heptane. The precipitated resin was separated by filtration and dried under reduced pressure to give white powder resin. The yield was 9.5 g. This resin is referred to as resin 10. The resin 10 had a weight-average molecular weight of 11300, a degree of dispersion (Mw/Mn) of 1.94, and a protection degree of 20%.

Resin Synthesis Example 9

10.0 g of the above resin 1 was dissolved in 100 mL of tetrahydrofuran, and 0.64 g of sodium hydride was added thereto. The mixture was stirred at room temperature until the solution became uniform, and then 3.46 g of the compound 3 was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L of n-heptane. The precipitated resin was separated by filtration and dried under reduced pressure to give white powder resin. The yield was 9.2 g. This resin is referred to as resin 11. The resin 11 had a weight-average molecular weight of 9000, a degree of dispersion (Mw/Mn) of 2.01, and a protection degree of 37%.

Resin Synthesis Example 10

10.0 g of the above resin 1 was dissolved in 100 mL of tetrahydrofuran, and 0.96 g of sodium hydride was added thereto. The mixture was stirred at room temperature until the solution became uniform, and then 5.19 g of the compound 3 was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L of n-heptane. The precipitated resin was separated by filtration and dried under reduced pressure to give white powder resin. The yield was 10.5 g. This resin is referred to as resin 12. The resin 12 had a weight-average molecular weight of 9800, a degree of dispersion (Mw/Mn) of 2.21, and a protection degree of 53%.

Resin Synthesis Example 11

10.0 g of the resin 13 (weight-average molecular weight=7640, degree of dispersion (Mw/Mn)=1.93) was dissolved in 100 mL of tetrahydrofuran, and 0.48 g of sodium hydride was added thereto. The mixture was stirred at room temperature until the solution became uniform, and then 1.26 g of the above compound 1 was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L of n-heptane. The precipitated resin was separated by filtration and dried under reduced pressure to give white powder resin. The yield was 6.0 g. This resin is referred to as resin 14. The resin 14 had a weight-average molecular weight of 9970, a degree of dispersion (Mw/Mn) of 1.70, and a protection degree of 30.7%. The absorptivity coefficient was 1.67 $\mu m^{-1}$.

Comparative Resin Synthesis Example 1

15.0 g of the resin 13 (weight–average molecular weight=7640, degree of dispersion (Mw/Mn)=1.93) was dissolved in 100 mL of tetrahydrofuran, and 0.88 g of sodium hydride was added thereto. The mixture was stirred at room temperature until the solution became uniform, and then 1.76 g of chloromethyl methyl ether (manufactured by Tokyo Kasei Kogyo Co., Ltd.) was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L of n-heptane. The precipitated resin was separated by filtration and dried under reduced pressure to give white powder resin. The yield was 5.0 g. This resin is referred to as resin 15. The resin 15 had a weight-average molecular weight of 14000, a degree of dispersion (Mw/Mn) of 2.14, and a protection degree of 40.7%. The absorptivity coefficient was 1.73 $\mu m^{-1}$.

Comparative Resin Synthesis Example 2

10.0 g of the resin 13 (weight-average molecular weight=7640, degree of dispersion (Mw/Mn)=1.93) was dissolved in 100 mL of tetrahydrofuran, and 0.48 g of sodium hydride was added thereto. The mixture was stirred at room temperature until the solution became uniform, and then 1.035 g of chloromethyl methyl ether (manufactured by Tokyo Kasei Kogyo Co., Ltd.) was added dropwise thereto. After stirring at room temperature for 12 hours, the precipitated salt was filtered off. The resulting filtrate was dropped into 1 L of water. The precipitated resin was separated by filtration, dried under reduced pressure, dissolved in tetrahydrofuran, and dropped into 1 L of n-heptane. The precipitated resin was separated by filtration and dried under reduced pressure to give white powder resin. The yield was 6.0 g. This resin is referred to as resin 16. The resin 16 had a weight-average molecular weight of 8850, a degree of dispersion (Mw/Mn) of 1.76, and a protection degree of 27.7%. The absorptivity coefficient was 1.73 $\mu m^{-1}$.

The general formulae representing the resins 1 to 16 are shown in the following formulae 14A and 15A:

Formula 14A

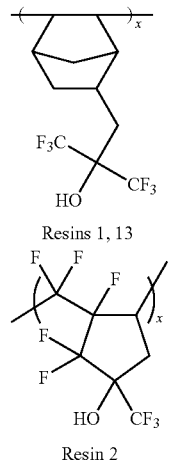

Resins 1, 13

Resin 2

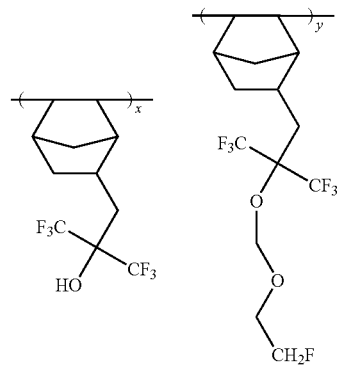

Resins 3, 4, 5, 14

-continued

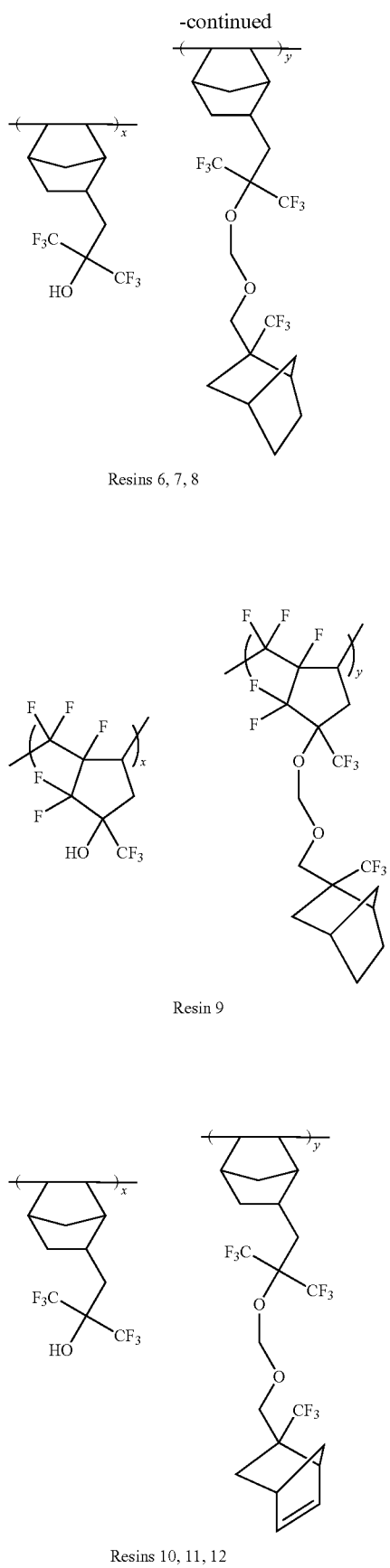

Resins 6, 7, 8

Resin 9

Formula 15A

Resins 10, 11, 12

-continued

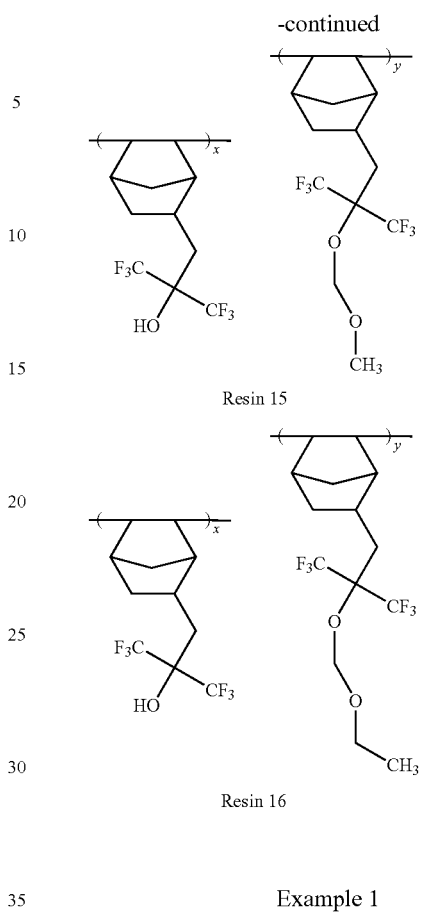

Resin 15

Resin 16

Example 1

Confirmation of the Light Exposure Resolution of a Positive Resist Composition

The resolution of a positive resist composition using the resin 3 was confirmed by exposure to an ArF excimer laser light. The resolution and exposure amount are shown in Table 1. The following acid generator and nitrogen-containing compound besides the resin were used to prepare the resist composition.

| | |
|---|---|
| Resin 3 | 100 parts by weight |
| Acid generator: TPS-PFBS (triphenyl sulfonium perfluorobutane sulfonate) | 3.0 parts by weight |
| Nitrogen-containing compound: triisopropanol amine | 0.1 part by weight |
| Solvent: MAK (methyl amyl ketone) | 1250 parts by weight |

Example 2

Confirmation of the Light Exposure Resolution of a Positive Resist Composition

The resolution of a positive resist using the resin 6 was confirmed by exposure to an ArF excimer laser light. The resolution and exposure amount are shown in Table 1. The following acid generator and nitrogen-containing compound besides the resin were used to prepare the resist composition.

| | | | |
|---|---|---|---|
| Resin 6 | | 100 | parts by weight |
| Acid generator: TPS-PFBS | | 3.0 | parts by weight |
| Nitrogen-containing compound: triisopropanol amine | | 0.1 | part by weight |
| Solvent: MAK | | 1250 | parts by weight |

Example 3

Confirmation of the Light Exposure Resolution of a Positive Resist Composition

The resolution of a positive resist using the resin 10 was confirmed by exposure to an ArF excimer laser light. The resolution and exposure amount are shown in Table 1. The following acid generator and nitrogen-containing compound besides the resin were used to prepare the resist composition.

| | | |
|---|---|---|
| Resin 10 | 100 | parts by weight |
| Acid generator: TPS-PFBS | 3.0 | parts by weight |
| Nitrogen-containing compound: triisopropanol amine | 0.1 | part by weight |
| Solvent: MAK | 1250 | parts by weight |

Example 4

Confirmation of the Light Exposure Resolution of a Positive Resist Composition

The resolution of a positive resist using the resin 9 was confirmed by exposure to an $F_2$ excimer laser light. The resolution and exposure amount are shown in Table 1. The following acid generator and nitrogen-containing compound besides the resin were used to prepare the resist composition.

| | | |
|---|---|---|
| Resin 9 | 100 | parts by weight |
| Acid generator: TPS-PFBS | 3.5 | parts by weight |
| Nitrogen-containing compound: triisopropanol amine | 0.1 | part by weight |
| Solvent: PGMEA (propylene glycol monomethyl ether acetate) | 1250 | parts by weight |

TABLE 1

| | Resist thickness (nm) | PB/PEB temperature (° C.) | Resolution (nm) by exposure to ArF and $F_2$ | Sensitivity (mJ/cm$^2$) by exposure to ArF and $F_2$ |
|---|---|---|---|---|
| Example 1 | 196 | 90/110 | 130 | 20 |
| Example 2 | 170 | 90/110 | 130 | 11 |
| Example 3 | 170 | 90/110 | 130 | 24 |
| Example 4 | 150 | 110/110 | 90 | 37 |

Example 5

100 parts by weight of the resin 14 obtained in Resin Synthesis Example 11 as component (A), 3.0 parts by weight of triphenyl sulfonium perfluorobutane sulfonate as component (B), and 0.1 part by weight of triisopropanol amine as component (C) were dissolved in 1150 parts by weight of propylene glycol monomethyl ether acetate to prepare a positive resist composition.

An organic anti-reflective film composition "AR-19" (trade name, manufactured by Shipley Company) was then applied onto a silicon wafer by using a spinner and baked to dry at 215° C. for 60 seconds on a hot plate thereby forming an organic anti-reflective film of 82 nm in thickness. The positive resist composition was then applied by a spinner onto the anti-reflective film and pre-baked (PAB) to dry at 110° C. for 90 seconds on a hot plate, whereby a resist layer of 200 nm in thickness was formed.

The resist layer was then irradiated selectively via a mask pattern (binary) with an ArF excimer laser (193 nm) by an ArF light exposure apparatus NSR-S302 (NA (numerical aperture)=0.60, ⅔ orbicular zone, manufactured by Nikon Corporation).

The resist layer was then subjected to PEB treatment under conditions of 90° C. and 90 seconds, then developed by puddling for 60 seconds with 2.38 wt % aqueous tetramethylammonium hydroxide solution at 23° C. to form a resist pattern. As a result, the limit resolution of a line and space upon exposure to such a quantity of light as to transfer a 130 nm mask at a level of 130 nm was 120 nm. The sensitivity upon formation of the 130 nm line and space at 1:1 was 20 mJ/cm$^2$.

Example 6

A positive resist composition was prepared to form a resist pattern in the same manner as in Example 5 except that the amount of the component (B) was changed to 2.0 parts by weight, the PEB conditions were changed to 90° C. and 60 seconds, and the development time was changed to 30 seconds. As a result, the limit resolution of a line and space upon exposure to such a quantity of light as to transfer a 130 nm mask at a level of 130 nm was 110 nm. The sensitivity upon formation of the 130 nm line and space at 1:1 was 52 mJ/cm$^2$.

Comparative Example 1

100 parts by weight of the resin 15 obtained in Comparative Resin Synthesis Example 1 as component (A), 3.0 parts by weight of triphenyl sulfonium perfluorobutane sulfonate as component (B), and 0.1 part by weight of triisopropanol amine as component (C) were dissolved in 1150 parts by weight of propylene glycol monomethyl ether acetate to prepare a positive resist composition.

An organic anti-reflective film composition "AR-19" (trade name, manufactured by Shipley Company) was then applied onto a silicon wafer by using a spinner and baked to dry at 215° C. for 60 seconds on a hot plate thereby forming an organic anti-reflective film of 82 nm in thickness. The positive resist composition was then applied by a spinner onto the anti-reflective film and pre-baked (PAB) at 110° C. for 90 seconds on a hot plate, whereby a resist layer of 200 nm in thickness was formed.

The resist layer was then irradiated selectively via a mask pattern (binary) with an ArF excimer laser (193 nm) by an ArF light exposure apparatus NSR-S302 (NA (numerical aperture)=0.60, ⅔ orbicular zone, manufactured by Nikon Corporation).

The resist layer was then subjected to PEB treatment under conditions of 90° C. and 90 seconds, then developed by puddling for 60 seconds with 2.38 wt % aqueous tetramethylammonium hydroxide solution at 23° C. to form a resist pattern. As a result, the limit resolution of a line and space upon exposure to such a quantity of light as to transfer a 130 nm mask at a level of 130 nm was 120 nm. The sensitivity upon formation of the 130 nm line and space at 1:1 was 20 mJ/cm$^2$.

Comparative Example 2

A positive resist composition was prepared to form a resist pattern in the same manner as in Example 5 except that the amount of the component (B) was changed to 2.0 parts by weight, the PEB conditions were changed to 90° C. and 60 seconds, and the development time was changed to 30 seconds, but the resist pattern did not show resolution.

Comparative Example 3

100 parts by weight of the resin 16 obtained in Comparative Resin Synthesis Example 2 as component (A), 3.0 parts by weight of triphenyl sulfonium perfluorobutane sulfonate as component (B), and 0.1 part by weight of triisopropanol amine as component (C) were dissolved in 1150 parts by weight of propylene glycol monomethyl ether acetate to prepare a positive resist composition.

An organic anti-reflective film composition "AR-19" (trade name, manufactured by Shipley Company) was then applied onto a silicon wafer by using a spinner and baked by drying at 215° C. for 60 seconds on a hot plate thereby forming an organic anti-reflective film of 82 nm in thickness. The positive resist composition was then applied by a spinner onto the anti-reflective film and pre-baked (PAB) at 110° C. for 90 seconds on a hot plate, whereby a resist layer of 200 nm in thickness was formed.

The resist layer was then irradiated selectively via a mask pattern (binary) with an ArF excimer laser (193 nm) by an ArF light exposure apparatus NSR-S302 (NA (numerical aperture)=0.60, ⅔ orbicular zone, manufactured by Nikon Corporation).

The resist layer was subjected to PEB treatment under conditions of 90° C. and 90 seconds, then developed by puddling for 60 seconds with 2.38 wt % aqueous tetramethylammonium hydroxide solution at 23° C. to form a resist pattern. As a result, the limit resolution of a line and space upon exposure to such a quantity of light as to transfer a 130 nm mask at a level of 130 nm was 120 nm. The sensitivity upon formation of the 130 nm line and space at 1:1 was 14 mJ/cm².

Comparative Example 4

A positive resist composition was prepared to form a resist pattern in the same manner as in Example 5 except that the amount of the component (B) was changed to 2.0 parts by weight, the PEB conditions were changed to 90° C. and 60 seconds, and the development time was changed to 30 seconds. As a result, the limit resolution of a line and space upon exposure to such a quantity of light as to transfer a 130 nm mask at a level of 130 nm was 110 nm. The sensitivity upon formation of the 130 nm line and space at 1:1 was 30 mJ/cm².

The absorptivity coefficients for light having a wavelength of 157 nm in Resin Synthesis Examples 11 and Resin Comparative Synthesis Examples 1 to 2 were measured in the following manner. First, the resin was dissolved in propylene glycol monomethyl ether acetate (PGMEA), and the resulting resin solution was applied onto a magnesium fluoride wafer and then heated at 110° C. for 90 seconds to form a resin coating of 200 nm in thickness. The resin coating was irradiated with light having a wavelength of 157 nm by a vacuum ultraviolet spectrophotometer VUV-200 (manufactured by JASCO Corporation) to determine absorptivity coefficient (μm⁻¹).

The resolutions in Examples 1 to 3, 5, and 6, and Comparative Examples 1 to 4 were confirmed by using an ArF excimer laser (193 nm), and thus significant difference thereamong was hardly observed. However, when resolution was confirmed with an $F_2$ excimer laser (157 nm), each resin used in Examples 1 to 6 had a higher content of fluorine atoms than in each resin used in Comparative Examples 1 to 4, thus showing higher transparency to an $F_2$ excimer laser light. Accordingly, each resin in the Examples can be used preferably in lithography using an $F_2$ excimer laser light. As one example, a 90 nm line and space pattern is resolved in lithography using an $F_2$ excimer laser light in Example 4.

INDUSTRIAL APPLICABILITY

As described above, the photoresist composition according to the present invention is useful for patterning of a semiconductor integrated circuit by lithography, and is suitable for fine patterning with a light source of a wavelength of 300 nm or less, especially KrF, ArF, and $F_2$ excimer lasers, particularly an $F_2$ excimer laser. The low-molecular compound and high-molecular compound of the present invention are useful for constituting the photoresist composition, and are particularly preferable in the photoresist composition excellent in transparency in fine patterning with a light source of a wavelength of 300 nm or less, especially KrF, ArF, and $F_2$ excimer lasers, particularly an $F_2$ excimer laser.

REFERENCES

Patent document 1: International publication WO 00/67072 Pamphlet
Patent document 2: Japanese Patent Application Laid-open No. 2002-90997
Patent document 3: International publication WO 02/64648 Pamphlet
Patent document 4: International publication WO 02/65212 Pamphlet
Patent document 5: Japanese Patent Application Laid-open No. 2002-333715
Non-patent document 1: M. K. Crawford, et al., "New Material for 157 nm Photoresists: Characterization and Properties" Proceedings of SPIE, Vol. 3999, (2000) pp357-364
Non-patent document 2: Shun-ichi Kodama, et al., "Synthesis of Novel Fluoropolymer for 157 nm Photoresists by Cyclopolymerization" Proceedings of SPIE, Vol. 4690, (2000) pp76-83

The invention claimed is:

1. A photoresist composition comprising:
(A) a base resin component having alkali-solubility changed by the action of an acid; and (B) an acid generator for generating an acid by irradiation with radiation rays, wherein the base resin component (A) comprises a compound having an alkali-soluble site (i), at least a part of the alkali-soluble site (i) is protected with (ii) a halogen atom-containing acetal type dissolution inhibiting group, and the dissolution inhibiting group (ii) ) is a group represented by the following general formula (1):

$$-O-C(R^1)(R^2)-O-R^3 \quad (1)$$

wherein $R^1$ and $R^2$ independently represent a hydrogen atom or a lower alkyl group, and $R^3$ is a group represented by the following general formula (2):

$$-[C(R^5)(R^6)]_n-R^4 \quad (2)$$

wherein $R^4$ is a halogen-containing norbornenyl group, $R^5$ and $R^6$ independently represent a hydrogen atom or a lower alkyl group, and n is 0 or an integer of 1 to 3, wherein the alkali-soluble site (i) is at least one member selected from the group consisting of an alcoholic hydroxyl group and a hydroxyl group of a carboxyl group.

2. The photoresist composition according to claim 1, wherein the alcoholic hydroxyl group is a fluorine-containing hydroxyl group.

3. The photoresist composition according to claim 1 or 2 wherein the halogen is a fluorine atom.

4. A high-molecular compound for a photoresist composition,
wherein the high-molecular compound has an alkali-soluble site (i), at least a part of the alkali-soluble site (i) is protected with (ii) a halogen atom-containing acetal type dissolution inhibiting group, and the dissolution inhibiting group (ii) is a group represented by the following general formula (1):

$$\mathrm{-O-C(R^1)(R^2)-O-R^3} \tag{1}$$

wherein $R^1$ and $R^2$ independently represent a hydrogen atom or a lower alkyl group, and $R^3$ is a group represented by the following general formula (2):

$$\mathrm{-[C(R^5)(R^6)]_{\mathit{n}}-R^4} \tag{2}$$

wherein $R^4$ is a halogen-containing norbornenyl group, $R^5$ and $R^6$ independently represent a hydrogen atom or a lower alkyl group, and n is 0 or an integer of 1 to 3, wherein the alkali-soluble site (i) is at least one member selected from the group consisting of an alcoholic hydroxyl group and a hydroxyl group of a carboxyl group.

5. The high-molecular compound for a photoresist composition according to claim 4, wherein the alcoholic hydroxyl group is a fluorine-containing alcoholic hydroxyl group.

6. The high-molecular compound for a photoresist composition according to any one of claims 4 and 5, wherein the halogen is a fluorine atom.

* * * * *